United States Patent [19]

Thaler et al.

[11] Patent Number: 4,946,594

[45] Date of Patent: Aug. 7, 1990

[54] CROSSLINKED COPOLYMERS OF ALIPHATIC POLYESTER DIOLS AND DIANHYDRIDES

[75] Inventors: Warren A. Thaler, Flemington; W. S. Winston Ho; Guido Sartori, both of Annandale, all of N.J.

[73] Assignee: Exxon Research and Engineering Company, Florham Park, N.J.

[21] Appl. No.: 422,217

[22] Filed: Oct. 16, 1989

[51] Int. Cl.[5] .............................................. B01D 13/00
[52] U.S. Cl. .................................... 210/651; 210/654
[58] Field of Search ................ 210/634, 644, 649–654; 525/314

[56] References Cited

U.S. PATENT DOCUMENTS 4,248,984 2/1981 Bi et al. ................................ 525/314

Primary Examiner—Frank Sever
Attorney, Agent, or Firm—Ronald D. Hantman

[57] ABSTRACT

A crosslinked copolymer composition is derived from an aliphatic polyester, a dianhydride and a diicoyanate. The copolymer membrane has high thermal stability and good aromatic/saturate selectivity and permeability.

7 Claims, 2 Drawing Sheets

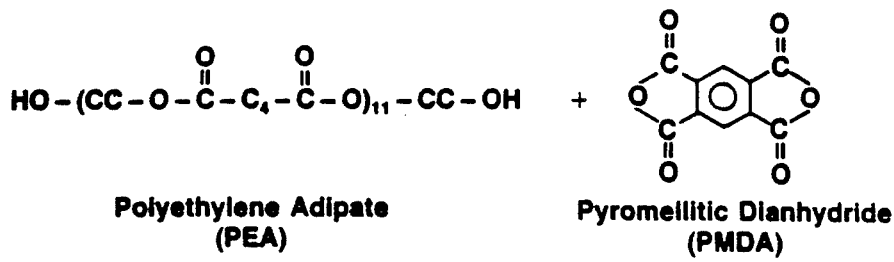
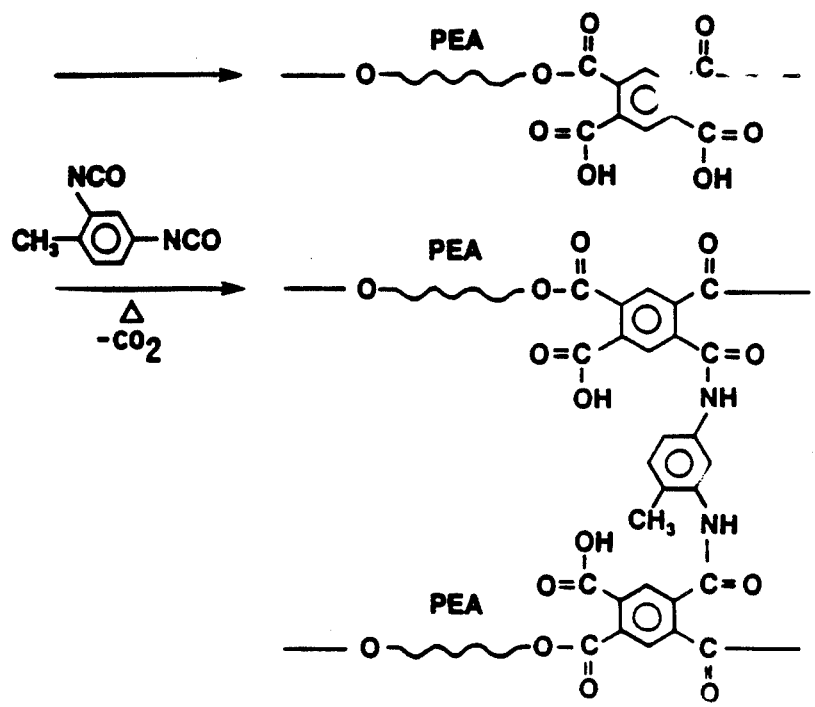
F I G. I

CROSSLINKED COPOLYMERS OF ALIPHATIC POLYESTER DIOLS AND DIANHYDRIDES

BACKGROUND

The present invention relates to a composition of matter for the separation of aromatics from saturates.

The use of membranes to separate aromatics from saturates has long been pursued by the scientific and industrial community and is the subject of numerous patents.

U.S. Pat. No. 3,370,102 describes a general process for separating a feed into a permeate stream and a retentate stream and utilizes a sweep liquid to remove the permeate from the face of the membrane to thereby maintain the concentration gradient driving force. The process can be used to separate a wide variety of mixtures including various petroleum fractions, naphthas, oils, hydrocarbon mixtures. Expressly recited is the separation of aromatics from kerosene.

U.S. Pat. No. 2,958,656 teaches the separation of hydrocarbons by type, i.e., aromatic, unsaturated, saturated, by permeating a portion of the mixture through a non-porous cellulose ether membrane and removing permeate from the permeate side of the membrane using a sweep gas or liquid. Feeds include hydrocarbon mixtures, e.g., naphtha (including virgin naphtha, naphtha from thermal or catalytic cracking, etc.).

U.S. Pat. No. 2,930,754 teaches a method for separating hydrocarbons, e.g., aromatic and/or olefins from gasoline boiling range mixtures, by the selective permeation of the aromatic through certain non-porous cellulose ester membranes. The permeated hydrocarbons are continuously removed from the permeate zone using a sweep gas or liquid.

U.S. Pat. No. 4,115,465 teaches the use of polyurethane membranes to selectively separate aromatics from saturates via pervaporation.

Compared to distillation, membrane permeation can lead to considerable energy savings. A membrane can separate a mixture of aromatics and saturates, e.g., a heavy cat naphtha, into a high-octane, mainly aromatic permeate and a high-cetane, mainly saturated retentate. Both permeate and retentate are more valuable than the starting heavy cat naphtha.

SUMMARY OF THE INVENTION

The present invention is a composition of matter and its use in a process for separating aromatics from feeds which are mixtures of aromatics and non-aromatics. The composition is formed into a membrane which includes a crosslinked copolymer composition wherein the copolymer is derived from an aliphatic polyester diol and a dianhydride. The aliphatic polyester may be a polyadipate, a polysuccinate, a polymalonate, a polyoxalate or a polyglutarate. Crosslinking can be accomplished by a variety of methods. Preferably, the copolymer is crosslinked by reaction with diisocyanates.

In a preferred embodiment, polyester is a polyethylene adipate or a polyethylene succinate, the dianhydride has between 8 and 20 carbons, and the diisocyanate has between 4 and 30 carbons.

In a preferred embodiment, the dianhydride is selected from the group consisting of pyromellitic dianhydride, 3,3',4,4'-benzophenone tetracarboxylic dianhydride, 4,4'-(hexafluoroisopropylidene)-bis-(phthalic anhydride), 4,4'-oxydiphthalic anhydride, diphenylsulfone-3,3',4,4'-tetracarboxylic dianhydride, and 3,3',4,4'-biphenyltetra-carboxylic dianhydride.

In a preferred embodiment, the diisocyanate is selected from the group consisting of 2,4-toluene diisocyanate (TDI), methylene diphenylisocyanate (MDI), methylene dichlorophenylisocyanate (dichloro-MDI), methylene dicyclohexylisocyanate ($H_{12}$-MDI), methylene dichlorocyclohexylisocyanate (dichloro-$H_{12}$-MDI), methylene bis(dichlorophenylisocyanate) (tetrachloro-MDI), and methylene bis(dichlorocyclohexylisocyanate) (tetrachloro-$H_{12}$-MDI).

The present invention also includes a method for separating aromatics from feeds which are mixtures of aromatics and non-aromatics which method comprises selectively permeating the aromatic hydrocarbon through a thin membrane including a crosslinked copolymer composition wherein the copolymer is derived from an aliphatic polyester diol, a dianhydride, and a diisocyante crosslinking reagent.

BRIEF DESCRIPTION OF THE DRAWINGS

FIG. 1 shows the synthesis and composition of toluene diisocyanate crosslinked polyethylene adipate-pyromellitic dianhydride copolymer of the preferred embodiment.

DESCRIPTION OF THE PREFERRED EMBODIMENT

Figure 2:
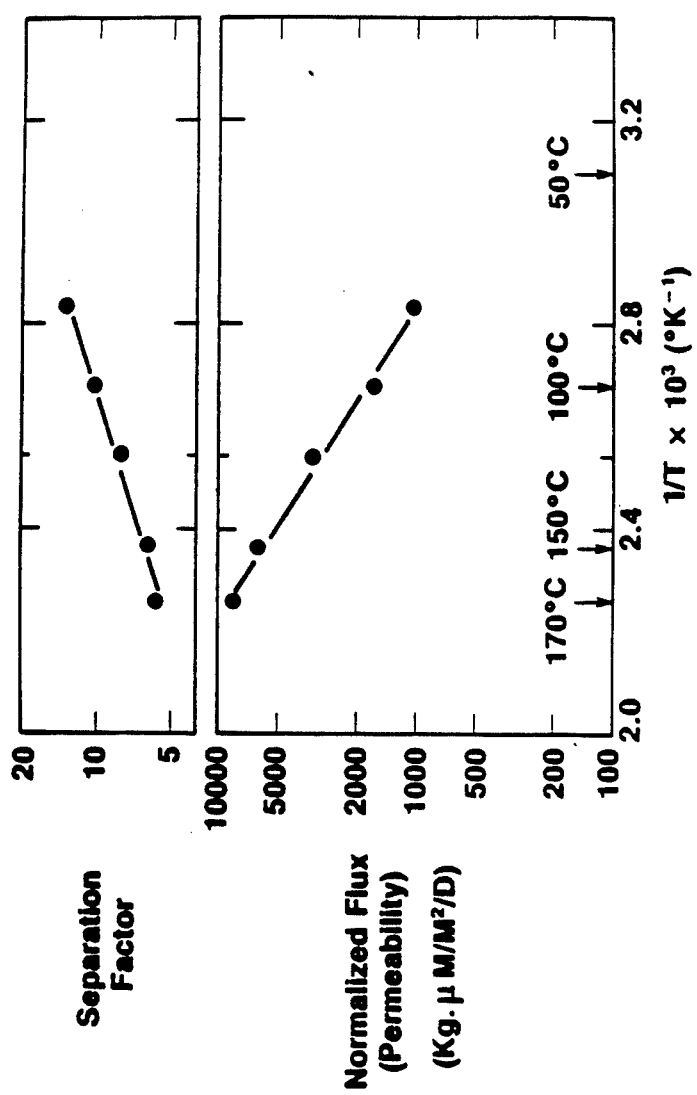
FIG. 2 shows the toluene/isooctane selectivity and permeability for a membrane of the present invention.

The present invention is new copolymers for membranes to separate aromatics from feed streams of aromatics and non-aromatics.

The new copolymers contain aliphatic polyester soft segments and hard segments derived from the dianhydride and the diisocyanate crosslinking reagent. FIG. 1 shows the synthesis and composition of the copolymer containing polyethylene adipate soft segment and crosslinked hard segment. In the synthesis, one mole of polyethylene adipate diol with a molecular weight of 2000 reacts with one mole of pyromellitic dianhydride (PMDA) to make a copolymer. The copolymer is then dissolved in dimethyl formamide (DMF) and 2,4-toluene diisocyanate (TDI) (at 0.5 mole to each mole of PMDA) is added to the solution. The new copolymer membrane can be prepared by casting the solution on a glass plate, or a porous support, adjusting the thickness by means of a casting knife, and drying the membrane first at room temperature to remove most of the solvent, then at 160° C. overnight to complete the crosslinking of polymer chains with TDI. The membrane is then removed from the glass plate via soaking in water. Finally, this membrane is then dried at 120° C. overnight.

The new membranes can be used for the separation of aromatics from saturates. In our separation experiments, the membranes are employed to separate a mixture containing toluene and isooctane in a pervaporation apparatus. The initial mixture contains about equal weights of the two hydrocarbons. The pervaporation apparatus is a cell, separated into two compartments by a porous metal plate, on which the membrane is supported. During a pervaporation experiment the toluene-isooctane mixture is circulated through the upper compartment at the desired temperature. The lower compartment is kept at reduced pressure. The permeate is collected in a trap cooled with dry ice-acetone or isopropanol and periodically analyzed by gas chromatography.

The membranes are useful for the separation of aromatics from saturates in petroleum and chemical streams, and have been found to be particularly useful for the separation of large substituted aromatics from saturates as are encountered in heavy cat naphtha streams. Other streams which are also suitable feed streams for aromatics from saturates separation are intermediate cat naphtha streams boiling at 93–160° C., light aromatics content streams boiling in the $C_5$–150° C. range, light catalytic cycle oil boiling in the 200–345° C. range as well as streams in chemical plants which contain recoverable quantities of benzene, toluene, xylenes (BTX) or other aromatics in combination with saturates. The separation techniques which may successfully employ the membranes of the present invention include perstraction and pervaporation.

Perstraction involves the selective dissolution of particular components contained in a mixture into the membrane, the diffusion of those components through the membrane and the removal of the diffused components from the downstream side of the membrane by the use of a liquid sweep stream. In the perstractive separation of aromatics from saturates in petroleum or chemical streams (particularly heavy cat naphtha streams) the aromatic molecules present in the feedstream dissolve into the membrane film due to similarities between the membrane solubility parameter and those of the aromatic species in the feed. The aromatics then permeate (diffuse) through the membrane and are swept away by a sweep liquid which is low in aromatics content. This keeps the concentration of aromatics at the permeate side of the membrane film low and maintains the concentration gradient which is responsible for the permeation of the aromatics through the membrane.

The sweep liquid is low in aromatics content so as not to itself decrease the concentration gradient. The sweep liquid is preferably a saturated hydrocarbon liquid with a boiling point much lower or much higher than that of the permeated aromatics. This is to facilitate separation, as by simple distillation. Suitable sweep liquids, therefore, would include, for example, $C_3$ to $C_6$ saturated hydrocarbons and lube basestocks ($C_{15}$–$C_{20}$).

The perstraction process is run at any convenient temperature, preferably as low as possible.

The choice of pressure is not critical since the perstraction process is not dependent on pressure, but on the ability of the aromatic components in the feed to dissolve into and migrate through the membrane under a concentration driving force. Consequently, any convenient pressure may be employed, the lower the better to avoid undesirable compaction, if the membrane is supported on a porous backing, or rupture of the membrane, if it is not.

If $C_3$ or $C_4$ sweep liquids are used at 25° C. or above in liquid state, the pressure must be increased to keep them in the liquid phase.

Pervaporation, by comparison, is run at generally higher temperatures than perstraction and relies on vacuum on the permeate side to evaporate the permeate from the surface of the membrane and maintain the concentration gradient driving force which drives the separation process. As in perstraction, the aromatic molecules present in the feed dissolve into the membrane film, migrate through said film and emerge on the permeate side under the influence of a concentration gradient. Pervaporative separation of aromatics from saturates can be performed at a temperature of about 25° C. for the separation of benzene from hexane but for separation of heavier aromatic/saturate mixtures, such as heavy cat naphtha, higher temperatures of at least 80° C. and higher, preferably at least 100° C. and higher, more preferably 120° C. and higher should be used. Temperatures of about 170° C. have been successfully used with membranes of the present invention, the maximum upper limit being that temperature at which the membrane is physically damaged. Vacuum on the order of 1–50 mm Hg is pulled on the permeate side. The vacuum stream containing the permeate is cooled to condense out the highly aromatic permeate. Condensation temperature should be below the dew point of the permeate at a given vacuum level.

The membrane itself may be in any convenient form utilizing any convenient module design. Thus, sheets of membrane material may be used in spiral wound or plate and frame permeation cell modules. Tubes and hollow fibers of membranes may be used in bundled configurations with either the feed or the sweep liquid (or vacuum) in the internal space of the tube or fiber, the other material obviously being on the other side.

When the membrane is used in a hollow fiber configuration with the feed introduced on the exterior side of the fiber, the sweep liquid flows on the inside of the hollow fiber to sweep away the permeated highly aromatic species, thereby maintaining the desired concentration gradient. The sweep liquid, along with the aromatics contained therein, is passed to separation means, typically distillation means, however, if a sweep liquid of low enough molecular weight is used, such as liquefied propane or butane, the sweep liquid can be permitted to simply evaporate, the liquid aromatics being recovered and the gaseous propane or butane (for example) being recovered and reliquefied by application of pressure or lowering of temperature.

The new copolymer composition of the present invention comprises the soft segment of an aliphatic polyester and the hard segment derived from a dianhydride and a diisocyanate. The aliphatic polyester may be a polyadipate, a polysuccinate, a polymalonate, a polyoxalate or a polyglutarate.

In a preferred embodiment, the aliphatic polyester is a polyethylene adipate or a polyethylene succinate, the dianhydride has between 8 and 20 carbons, and the diisocyanate has between 4 and 30 carbons.

In a preferred embodiment, the dianhydride is selected from the group consisting of pyromellitic dianhydride, 3,3',4,4'-benzophenone tetracarboxylic dianhydride, 4,4'-(hexafluoroisopropylidene)-bis-(phthalic anhydride), 4,4'-oxydiphthalic anhydride, diphenylsulfone-3,3',4,4'-tetracarboxylic dianhydride, and 3,3',4,4'-biphenyltetra-carboxylic dianhydride.

In a preferred embodiment, the diisocyanate is selected from the group consisting of 2,4-toluene diisocyanate (TDI), methylene diphenylisocyanate (MDI), methylene dichlorophenylisocyanate (dichloro-MDI), methylene dicyclohexylisocyanate ($H_{12}$-MDI), methylene dichlorocyclohexylisocyanate (dichloro-$H_{12}$-MDI), methylene bis(dichlorophenylisocyanate) (tetrachloro-MDI), and methylene bis(dichlorocyclohexylisocyanate) (tetrachloro-$H_{12}$-MDI).

It has been observed that the new membranes from the new copolymer composition of the present invention can separate toluene from isooctane, showing good selectivity and permeability. The membrane has a high thermal stability of about 170° C. in pervaporation separation of the toluene/isooctane mixture. The present invention will be better understood by reference to the following examples which are offered by way of illustration and not limitation.

EXAMPLE

Synthesis of Toluene Diisocyanate Cross-linked Polyethylene Adipate-Pyromellitic Dianhydride Copolymer Membrane To 10 g (0.005 mole) of polyethylene adipate diol with a molecular weight of 2000 at about 80° C. under $N_2$ in a reactor was added 1.09 g (0.005 mole) of pyromellitic dianhydride (PMDA) with stirring. The temperature increased to about 100° C., and the stirring continued for about 6 hours at this temperature for polymerization. To the reactor content was added about 20 g of DMF with stirring. Then, the reactor content was cooled to room temperature overnight. Finally, about 0.44 g (0.0025 mole) of TDI was added to the reactor content to give the resulting solution with suitable consistency for solution casting in the preparation of membranes.

The resulting solution was centrifuged for about 5 minutes. Following centrifugation, a membrane was knife-cast onto a glass plate with a knife gap setting of 14 mils. DMF was allowed to evaporate from the membrane in a hood at ambient conditions over a period of about 17 hours. The membrane was then dried in an oven at 160° C. overnight to complete the cross-linking of polymer chains with TDI. The membrane was then removed from the glass plate by soaking it in a water bath. Finally, the membrane was dried at 120° C. overnight. The resulting membrane had a thickness of about 95 microns.

EXAMPLE 2

Pervaporation Results

The resulting membrane described in Example 1 was evaluated for aromatic/saturate separation with the feed mixture of 50 wt% toluene and 50 wt% isooctane in the pervaporation apparatus described above. FIG. 2 shows the toluene/isooctane selectivity and permeability for the copolymer membrane as a function of temperature. As shown in this figure, this copolymer membrane had good selectivity and permeability. This figure also shows that this copolymer membrane had a good thermal stability of about 170° C.

What is claimed is:

1. A method for separating aromatics from feeds which are mixtures of aromatics and non-aromatics which method comprises providing a thin membrane including a crosslinked copolymer composition wherein said copolymer is derived from an aliphatic polyester diol, a dianhydride, and a diisocyante crosslinking reagent, and said aliphatic polyester is a polyadipate, a polysuccinate, a polymalonate, a polyoxalate, or a polyglutarate and selectively permeating the aromatic through.

2. The method of claim 1 wherein said polyester is polyethylene adipate or polyethylene succinate.

3. The method of claim 1 wherein said dianhydride is an aromatic compound.

4. The method of claim 3 wherein said aromatic compound is selected from the group consisting of pyromellitic dianhydride 3,3', 4,4'-benzophenone tetracarboxylic dianhydride, 4,4'-(hexafluoroisopropylidene)-bis(phthalic anhydride), 4,4'-oxydiphthalic anhydride, diphenyl-sulfone-3,3',4,4'-tetracarboxylic dianhydride, and 3,3'-4,4'-diphenyltetra-carboxylic dianhydride.

5. The method of claim 1 wherein said diisocyante is selected from the group consisting of 2,4-toluene diisocyanate (TID), methylene diphenylisocyanate (MDI), methylene dichlorophenylisocyanate (dichloro-MDI), methylene dicyclohexylisocyanate ($H_{12}$-MDI), methylene dichlorocyclohexyl-isocyanate (dichloro-$H_{12}$-MDI), methylene bid(dichlorophenylisocyanate) (tetrachloro-MDI), and methylene bis(dichlorocyclohexylisocyanate) (tetrachloro-$H_{12}$-MDI).

6. The method of claim 1 wherein said diisocyanate is 2,4-toluene diisocyanate.

7. The method of claim 1 wherein said dianhydride is pyromellitic dianhydride.

* * * * *